United States Patent [19]

Sturm et al.

[11] Patent Number: 5,315,630

[45] Date of Patent: May 24, 1994

[54] POSITIONING DEVICE IN MEDICAL APPARATUS

[75] Inventors: Volker Sturm, Wiesloch-Schatthausen; Otto Pastyr, Leimen-St. Ilgen; Wolgang Schlegel, Heidelberg; Christoph Uihlein, Üerlingen; Thomas Mack, Altheim, all of Fed. Rep. of Germany

[73] Assignee: Bodenseewerk Geratetechnik GmbH, Uberlingen/Bodensee, United Kingdom

[21] Appl. No.: 29,015

[22] Filed: Mar. 10, 1993

[30] Foreign Application Priority Data

Mar. 11, 1992 [DE] Fed. Rep. of Germany ....... 4207632

[51] Int. Cl.$^5$ ............................................. G21K 5/10
[52] U.S. Cl. ............................................. 378/65; 378/68; 378/69; 378/205
[58] Field of Search ............... 378/64, 65, 62, 68, 378/69, 205, 206, 208, 209, 162, 163

[56] References Cited

U.S. PATENT DOCUMENTS

| | | | |
|---|---|---|---|
| 4,262,305 | 4/1987 | Renner | 378/205 X |
| 4,730,351 | 3/1988 | Hermann | 378/205 X |
| 5,039,867 | 8/1991 | Nishihara et al. | 378/65 X |

*Primary Examiner*—David P. Porta
*Attorney, Agent, or Firm*—Lee, Mann, Smith, McWilliams, Sweeney & Ohlson

[57] ABSTRACT

A body part such as a patient's head is positioned for treatment purposes by holding a treatment point defined relative to marks attached to the body part is held in a desired position. To this end, at least two picture signal generating sensors are aligned to observe the marks. A picture processing device for processing the pictures of the marks is provided to define marker points, which are determined by the marks and define the actual position of the body part. Furthermore, a signal processing and control device is provided for computing the actual position from the observed positions of the marker points, for comparing the actual position with a desired position and for generating actuating signals, which depend on the error between actual position and desired position. The actuating signals are applied to actuators, which engage the body part. Thereby the treatment point can be returned to the desired position, if it has deviated therefrom.

14 Claims, 6 Drawing Sheets

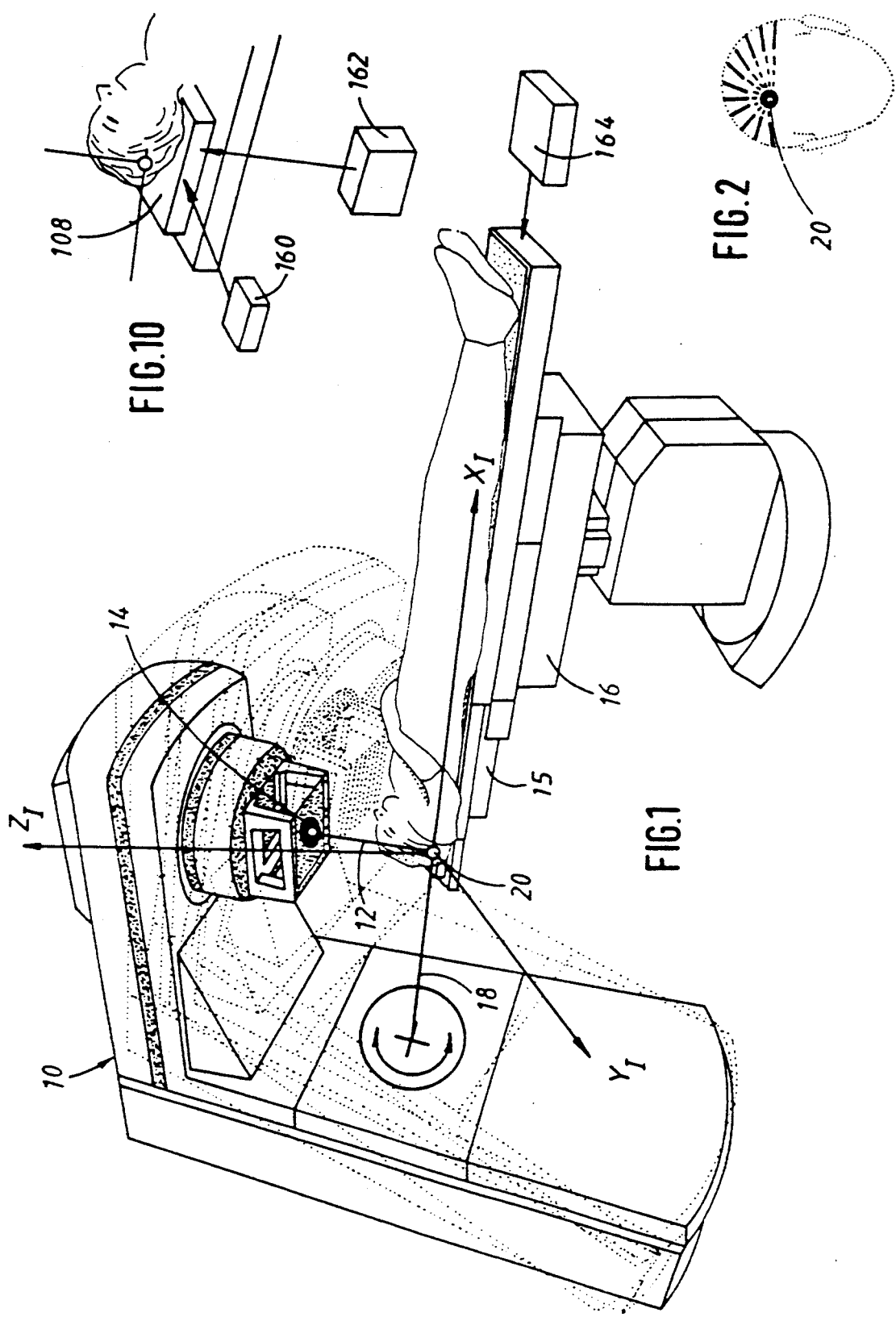

POSITIONING DEVICE IN MEDICAL APPARATUS

The invention relates to a device for positioning a body part of the human body for treatment with a medical apparatus, wherein marks are affixed to said body part at well-defined positions, the positioning of said body part causing an exactly defined treatment point to be maintained at a desired position.

In particular, the invention relates to the ray treatment of tumours in the brain by means of a ray treatmen apparatus. During such treatment, the ray from the ray treatment apparatus should hit the tumour with an accuracy of fractions of a millimeter. This counteracts any damage of the healthy tissue and utilizes the radiation optimally. With such ray treatment, it has been found advantageous, not to apply the whole dose in one treatment. Instead a number of smaller doses should be applied at intervals. Furthermore, it would be preferable to apply the radiation doses from different directions. Thereby, the radiation which also hits the surrounding healthy tissue is distributed within an enlarged region. Therefore, the risk of permanently damaging healthy tissue is reduced. The rays which emanate from the ray treatment apparatus during the application of the various doses have to intersect exactly in an iso-center in the region of the tumour to be ray treated. This requires, however, that the patient's head is positioned and aligned with corresponding accuracy.

In practice, a stereotactic procedure is used: A metal ring is attached to the patient's head by screwing it to bone of the cranium. An acrylic glass cylinder is connected with the metal ring. Metal wires are cast into the acrylic glass cylinder. These metal wires define a head-fixed coordinate system. A computer tomogram is made of the patient's head and of the acrylic glass cylinder with the metal wires. The metal wires are visible in the computer tomogram. The position of the tumour also appearing in the computer tomogram can then be determined, relative to the coordinate system defined by the metal wires, with an accuracy of fractions of a millimeter.

Then the tumour (treatment point), the position of which has been determined this way, is accurately aligned with the iso-center by means of an optical alignment system, the ray of the ray treatment apparatus passing always through this iso-center.

The prior art method for measuring and fixing the position of the patient's head is too time consuming and, therefore, not suitable for multiple applications.

It is an object of the invention to retain a patient's body part in a well-defined and reproducible position relative to an medical apparatus for the purpose of treating this body part.

It is a more specific object of the invention to hold the patient's head in a well-defined position relative to the ray of a ray treatment apparatus during fractionated ray treatment.

According to one aspect of the invention this object is achieved by at least two picture signal generating sensors, which are aligned to monitor said marks, picture processing means, to which said picture signals from said sensors are applied for processing pictures of said marks to fix marker points, which are determined by said marks and define the actual position of said body part, signal processing and controller means for computing the actual position of the body part from the observed position of said marker points, for comparing said actual position with a desired position, and for generating actuating signals, which depend on the error between said actual position and said desired position of said body part, and means for preventing treatment with misalignment between said apparatus and said body part, said actuating signals being applied to said preventing means.

According to the invention, the position and attitude of the patient's head or of some other body part is determined by detecting the marks by means of the sensors. A control loop serves to maintain the correct position. Surprisingly, it has been found, that a higher accuracy of positioning can be achieved in this way than by mechanical fixing. Instead of moving the head for aligning the treatment point with the iso-center, also the treatment ray can be deflected. In the case of emergency, the treatment apparatus can be disabled, if it is misaligned.

Preferably, each of the the sensors comprises means for generating a pixel matrix, in which the marks appear as two dimensional structures. The picture processing means are arranged to determine the centers of gravity of the thus obtained two-dimensional structures, these centers of gravity representing marker points.

The resolution of conventional sensors of this type is lower than the required positioning accuracy. If, however, the center of gravity of a two-dimensional structure detected by these sensors is formed by conventional means of pattern recognition, thus, so to say, forms a mean across the rather coarse raster, this center of gravity is defined with the required accuracy. Thus by scanning the extended marks, "marker points" of sub-pixel accuracy can be determined. These marker points define the actual position of the body part to be treated with sufficient accuracy.

The marks can be balls. Such balls appear, in the pixel matrix, as circular structures independently of the direction from which they are observed. In order to facilitate the picture processing, it is advantageous, if areas forming a contrast with said balls are provided behind said balls, as viewed from said sensors. Means for illuminating said balls from a plurality of directions may be provided.

For exactly positioning a patient's head relative to a ray treatment apparatus, the treatment point being located in a tumour to be treated, the device comprises an elongated ray treatment table defining a longitudinal direction and a carriage guided on said ray treatment table for horizontal movement in said longitudinal direction, said carriage being adapted to accommodate a patient. A head rest is separate from said ray treatment table and carriage and adapted to accommodate the patient's head and includes means for fixing the patient's head on said head rest. First and second actuator means, to which respective ones of said actuating signals are applied, engage said head rest to move said head rest relative to said ray treatment table. A third actuator means, to which a third one of said actuating signals is applied engages said carriage to move said carriage in said longitudinal direction. Said actuator means are arranged and controlled by said actuating signals to to return said patient's head to said desired position, if it has deviated from this desired position.

In this way, the patient's head is moved up and down and laterally. However there is no longitudinal stretching of the patient's neck.

According to a second aspect of the invention, a method for for positioning a body part of the human body for treatment with a medical apparatus, wherein marks are affixed to said body part at well-defined positions, the positioning of said body part causing an exactly defined treatment point to be maintained at a desired position, comprises the method steps of measuring the position of said marks by means of at least two picture generating sensors during a first treatment, when said body part to be treated is fixed in a predetermined desired position relative to said medical apparatus, whereby said sensors produce two-dimensional pictures of said marks, determining the centers of gravity of said images by picture processing in sensor-fixed coordinate systems, determining the position of said centers of gravity of said marks in an apparatus-fixed coordinate system from the centers of gravity of the pictures as a measure of a desired position of said body part, measuring the position of said marks during a subsequent treatment by means of the same sensors which are aligned in the same way as during said first treatment, determining the position deviation of the centers of gravity of the marks in the apparatus-fixed coordinate-system from the centers of gravity said pictures determined in said sensor-fixed coordinate systems, and generating actuating signals depending on said position deviation and correcting the position of said body part in response to said actuating signals.

An embodiment of the invention is described in greater detail hereinbelow with reference to the accompanying drawings.

FIG. 1 is a schematic-perspective illustration of a ray treatment apparatus for ray treating a brain tumour by means of a linear accelerator, the radiation dose being applied fractionatedly from different directions.

FIG. 2 illustrates the various directions of the ray, the ray always passing through an iso-center located within the tumour.

Figure 3:
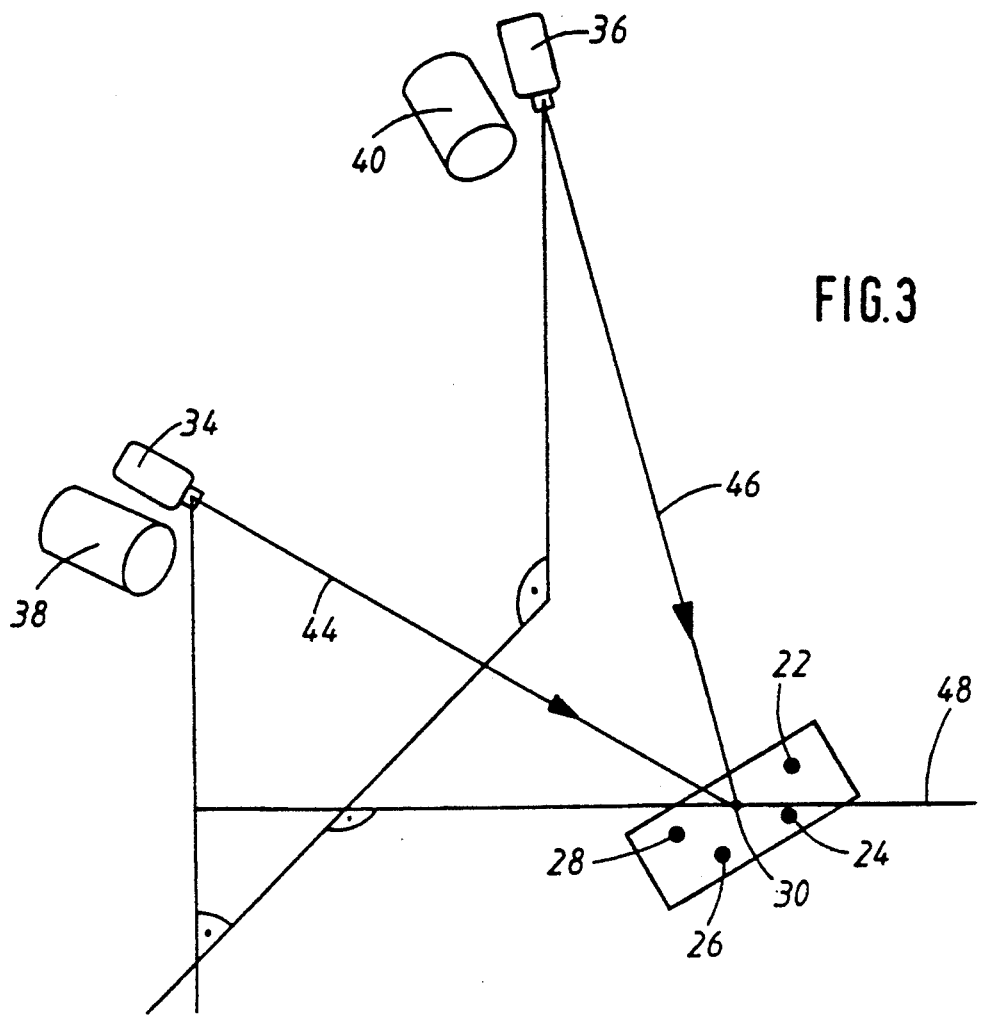

FIG. 3 illustrates schematically an arrangement with two picture signal generating sensors (cameras), which, by means of marks to be attached to the patient, permit a well-defined, once accurately measured position of the patient relative to the ray treatment apparatus to be reproduced, such that, during subsequent ray treatments, the ray of the ray treatment apparatus will hit the tumour again accurately.

Figure 4:
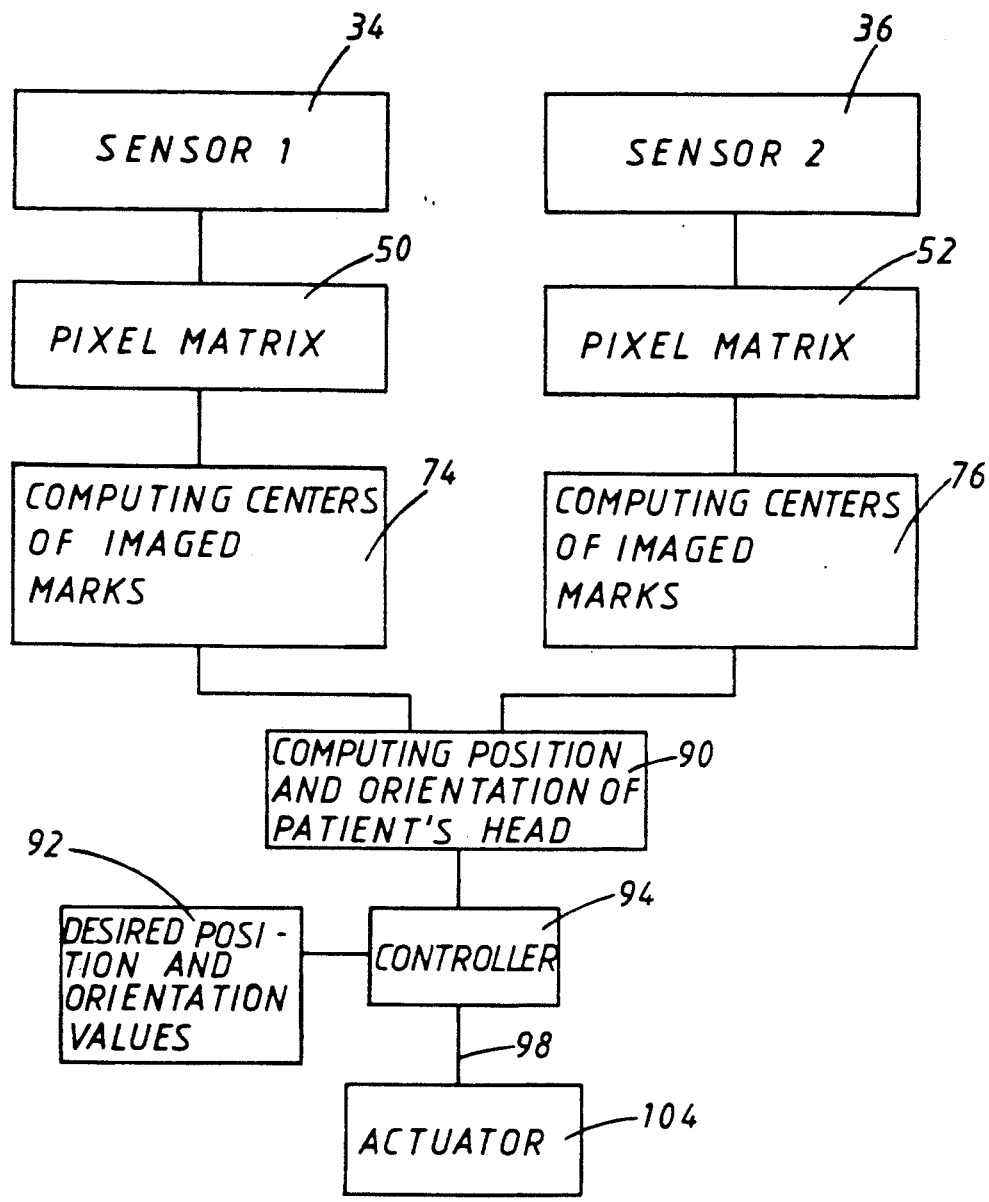

FIG. 4 is a diagram and shows schematically the individual steps of the picture and signal processing with an arrangement of FIG. 3.

Figure 5:
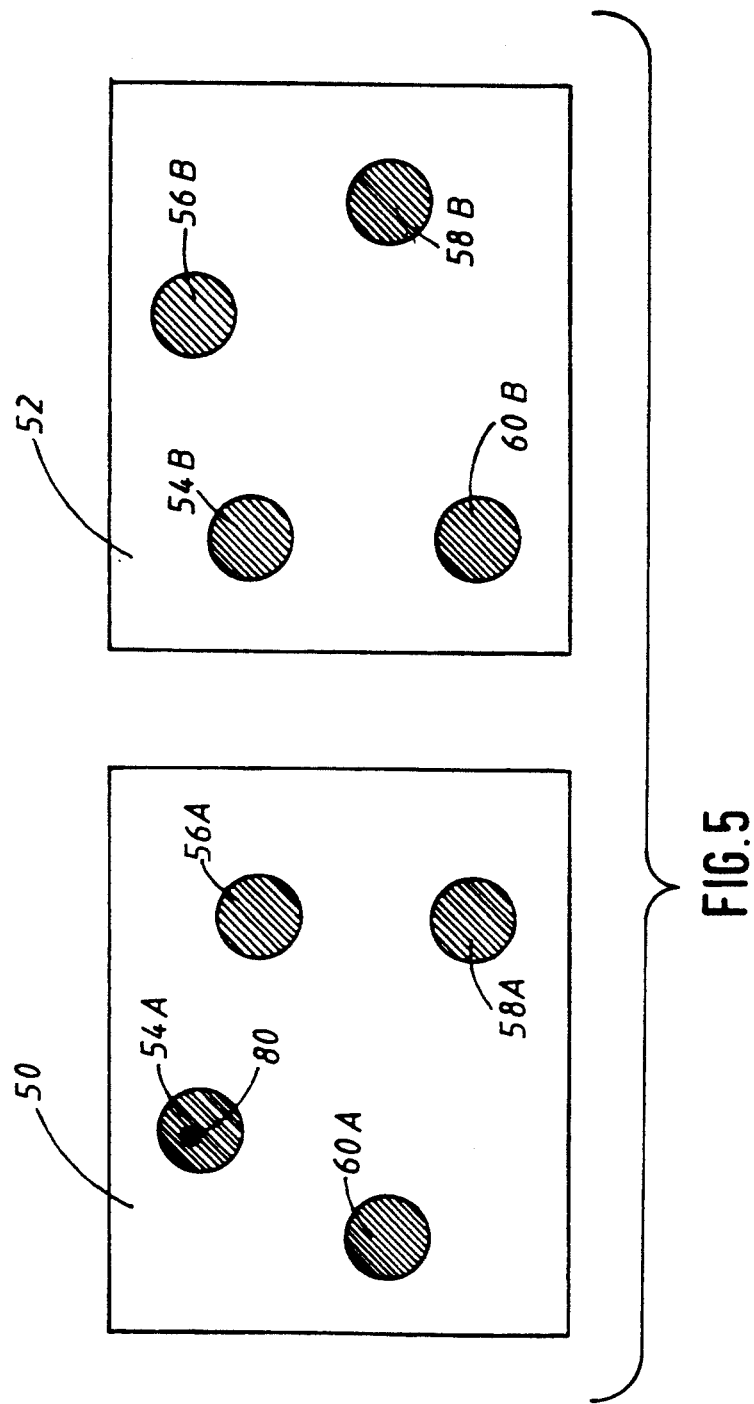

FIG. 5 is a schematic illustration of the pixel matrix provided by the sensors and illustrates the picture processing.

Figure 6:
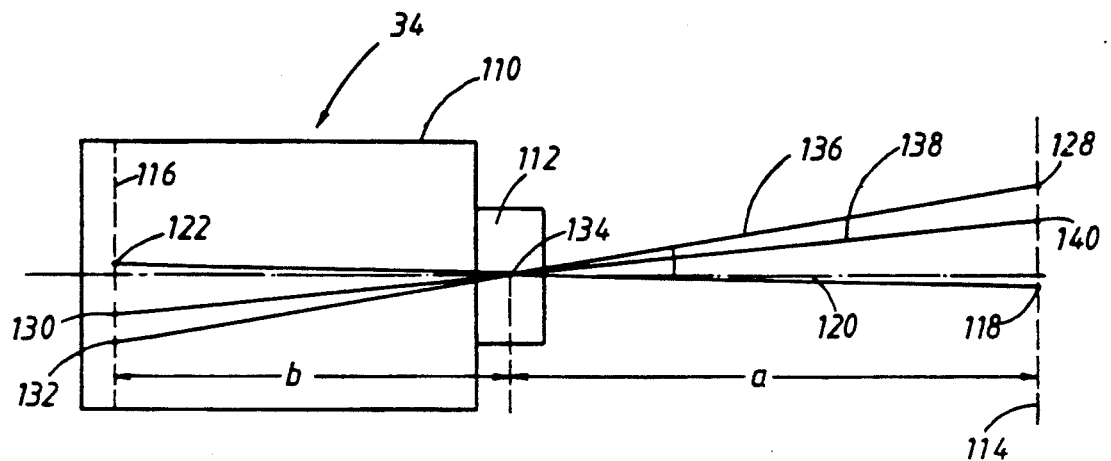

FIG. 6 is a schematic longitudinal sectional view of a sensor.

Figure 7:
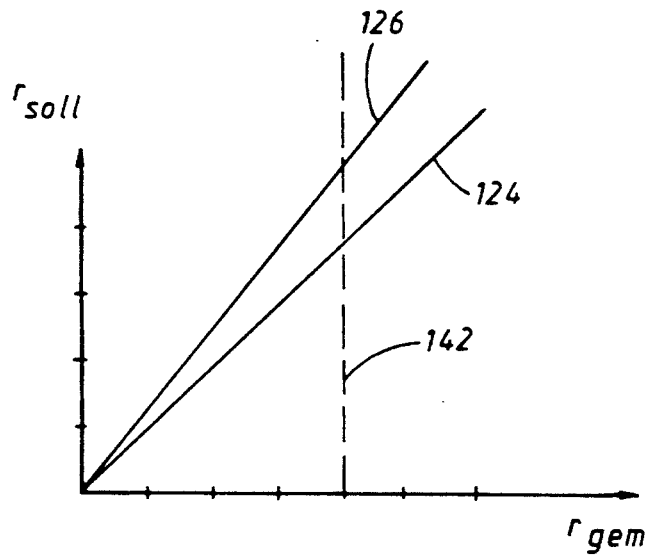

FIG. 7 illustrates, in an exaggerated representation, the characteristic of the aberrations of the imaging optical system of the sensor.

Figure 8:
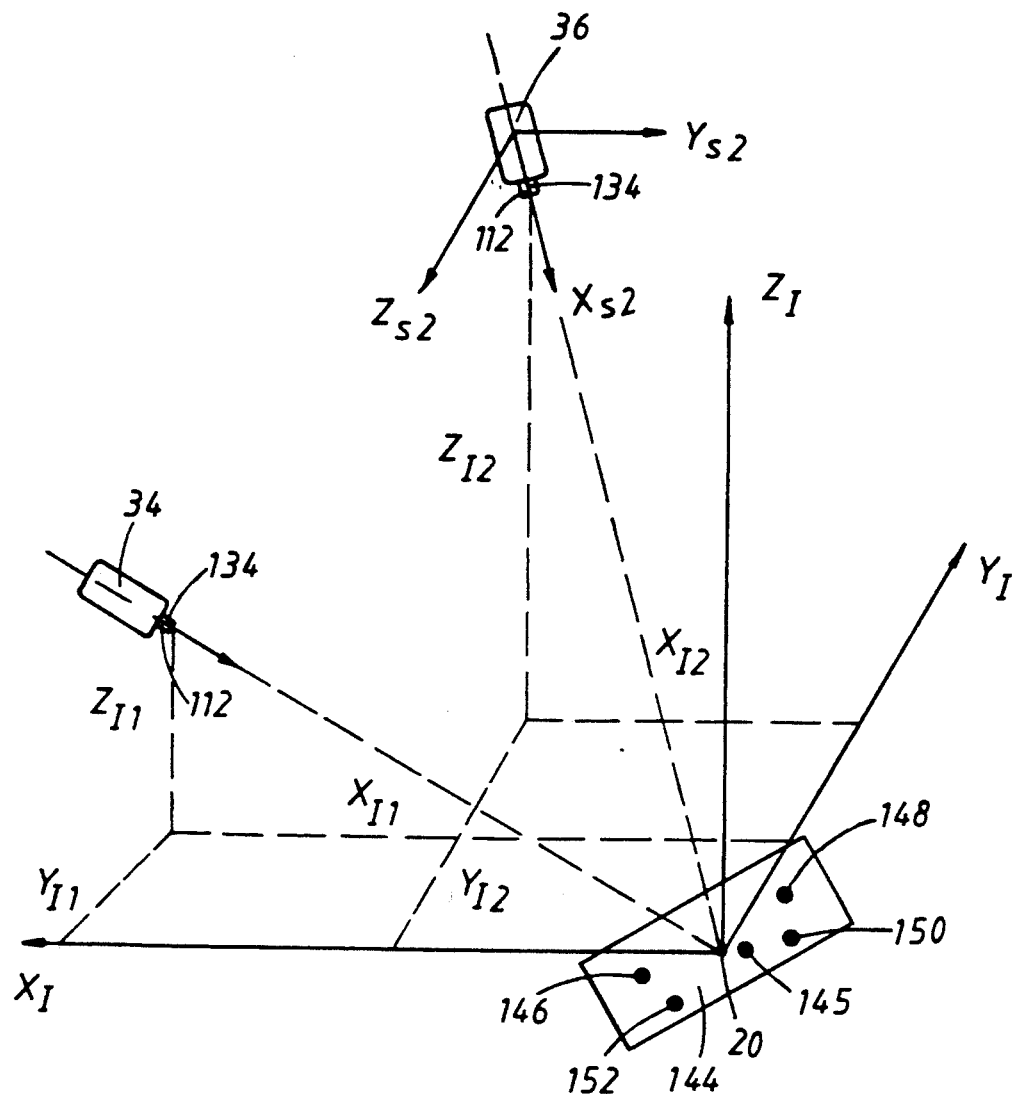

FIG. 8 illustrates the determination of the positions and orientations of the sensors by means of a reference body.

Figure 9:
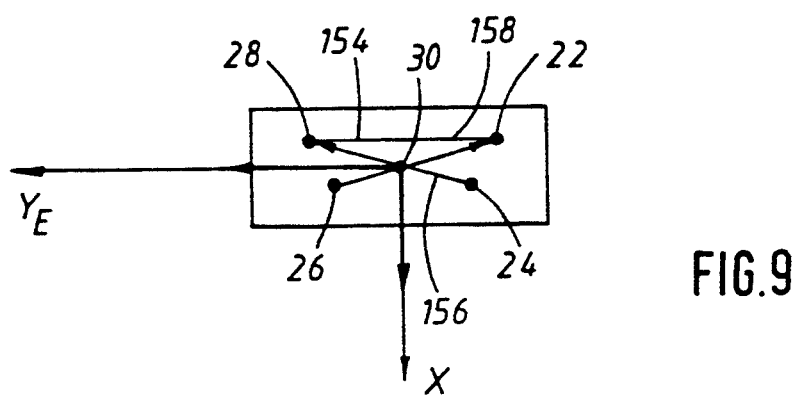

FIG. 9 shows the marks attached to the patient's head.

FIG. 10 shows the actuators by which the patient's head is moved into the desired position.

FIG. 1 schematically illustrates a ray treatment apparatus for ray treating a brain tumour. The ray treatment apparatus is designated by reference numeral 10. The ray treatment apparatus 10 generates a ray 12 of high-energy gamma secondary radiation. The cross section of the ray 12 is determined by a stop 14. A patient lies on a ray treatment table 16.

In order to ray treat a tumour consecutively from different directions and thereby to minimize the loading of the healthy tissue passed through by the ray, the ray treatment apparatus 10 is rotatable about an axis 18. The ray 12 intersects the axis 18 in an iso-center 20. The tumour has to be placed in this iso-center by appropriate adjustment of the ray treatment table. If this is the case, the ray will always pass through the tumour, also when the ray treatment apparatus is rotated about the axis 18, as indicated in FIG. 2.

At first, the exact position of the tumour to be ray treated in the patient's cranium is determined. This is a well known technique. A ring is attached to the patient's cranium. Acrylic glass bodies with metal wires are attached to the ring. The metal wires serve as marks. A computer tomogram or a NMR-tomogram of the patient's head with this ring is made. This tomogram shows the position of the tumour and the metal wires. The position of the tumour is then defined in a coordinate system represented by the metal wires.

During the first ray treatment, the patient's head to be ray treated is exactly aligned and fixed by means of stereotactic methods. Then the treatment point, thus, for example, the tumour is located exactly in the iso-center of the apparatus. The iso-center is a well-defined point in the apparatus-fixed coordinate system.

The problem now is to locate the patient's head exactly in this once measured position during subsequent treatments. This should be done without the described stereotactic contrivance and in essentially shorter time.

To this end, marks are attached to the patient's head prior to the first measurement. These marks have a reproducible position relative to the patient's cranium. In the described embodiment, these marks comprise dowels, which are fixed in the bone of the cranium. The marks can also be attached to a mouthpiece fitted to the patient's teeth.

During the first alignment described hereinbefore, these marks are observed by means of picture signal generating sensors 34, 36. The picture signal generating sensors 34 and 36 are a kind of video cameras. By this observation the initial alignment is measured. This defines a "desired position". During subsequent ray treatments, the marks are detected by the sensors 34 and 36, which are fixed in space. An actual position is determined from the picture information provided by the sensors 34 and 36. A control loop with actuators serves to move the patient's cranium into the desired position again.

FIG. 3 shows an example of such marks. A total of four such marks are provided here. These four marks 22, 24, 26 and 28 are located substantially in the four corners of a symmetric trapezoid. Numeral 30 designates the center of this trapezoid. The marks include light-colored balls, which are attached to the dowels and are placed in front of a dark background 32.

The marks are observed by two picture signal generating sensors 34 and 36. The marks are illuminated uniformly from all sides by lamps 38 and 40. In the illustrated embodiment, the two sensors are located in a vertical plane 44 at a horizontal distance of about 500 millimeters, and about 600 millimeters above the horizontal plane containing the marks 30. Their optical axes point substantially to the center of the trapezoid. The center 30 is located at a distance of about 500 millimeters from the vertical plane containing the sensors 34 and 36 and in the vertical plane of symmetry, orthogonal to this vertical plane, between the two sensors 34 and 36.

The geometry described above and the dimensions given are not critical. They give a clue to an arrangement, by which, in practice, a sufficiently accurate alignment of the patient can be achieved.

The processing of the picture information received from the sensors 34 and 36 is schematically illustrated in the diagram of FIG. 4.

The sensors 34 and 36 provide pixel matrices 50 and 52, respectively. Each picture element (pixel) of the picture detected by the respective sensor 34 or 36 provides a brightness value. FIG. 5 illustrates an example of the pixel matrices 50 and 52 provided by the sensors 34 and 36, respectively. In these pixel matrices, circular structures 54A, 56A, 58A, 60A, and 54B, 56B, 58B, 60B, respectively will be recognized as images of the marks 22, 24, 26, 28 and 30, respectively. The marks are balls. The images, therefore, are substantially circular independent of the direction from which the marks are observed.

The picture processing involves the following steps:

At first, the images of the marks are identified. This identification operation comprises the step of associating the various images of marks such as 54A with particular marks such as 22.

The pixels represent a rather coarse raster. The dimensions of a pixel projected into the plane of the marks are larger than the required positioning accuracy. Of course, also the dimensions of the marks themselves are substantially larger than the desired positioning accuracy. Therefore, the next step involves determining the centers of gravity. The centers of gravity of the objects identified as images of the marks are determined. The coordinates of these centers of gravity can be determined with essentially higher accuracy than one pixel length or hight.

Thus in order to achieve an accuracy of positioning of fractions of a millimeter, it is neither necessary to provide correspondingly small marks nor to sample the field of view with a resolution equal to the required accuracy. Relatively large marks are sufficient, though these marks ought to have a well-defined, regular shape. And sensors can be used which detect the picture with a relatively coarse raster.

Determining the centers of gravity is indicated by blocks 74 and 76 in FIG. 4.

Now, in the picture plane 78 points 80 are defined which represent the centers of gravity of the images of the marks. From the points 80 and the imaging characteristics of the optical systems 82 of the sensors 34 and 36, respectively, (including aberrations) it is possible to compute the ray 84 extending from the sensor 34 or 36 to the center of gravity of the mark (for example 22).

The computation of the rays is illustrated in FIG. 4 by the blocks 86 and 88. The computation of the position and attitude of the patient's head is illustrated by a block 90 in FIG. 4.

In order to achieve the required high accuracy, it is necessary to determine, at first, the individual imaging characteristics of each sensor. To this end, an exactly known test body is observed by the sensors through their optical systems, and the images of the test body produced by the optical systems are surveyed.

Furthermore, the location and the alignment of all sensors in the coordinate system of the ray treatment apparatus have to be exactly measured at short intervals (daily). To this end, a reference body is placed with its center at the iso-center 20. Marked axes of the reference body are aligned parallel to the axes the space-fixed coordinate system referenced to the ray treatment apparatus. The reference body bears five marks. These marks are also light-colored balls in front of a dark background. The position of the marks relative to the center of the reference body is exactly known. Then the the orientation and position of the sensor with three cartesian coordinates and three Eulerian angles with respect to the coordinate system is computed from the centers of gravity of the imaged marks.

Mathematically, it is advantageous, to compute the position and attitude of the sensor by means of the inverse function: The coordinates of the centers of gravity of the images are computed for a selected, estimated position and attitude of the sensor. As a rule, these computed coordinates of the centers of gravity deviate from the actually observed coordinates of the centers of gravity of the images. Then the the sum of the squared distances between the computed and the observed coordinates of the centers of gravity is computed. This squared distance sum is minimized by corrections of the estimated position and attitude of the sensor. A system of non-linear equations is obtained for these corrections. This system of equations is solved by linearization and iteration. Thereby, optimal values of the position and attitude of the sensors in the apparatus-fixed and reference body-fixed coordinate system.

During the first ray treatment, the patient's head is aligned by means of stereotactic procedures and fixed, as described above. Then the treatment center (tumour) is located exactly at the iso-center 20. In this position, the positions of the marks affixed to the cranium are determined in the apparatus-fixed coordinate system by means of the sensors 34 and 36. This is done as follows:

From the positions and attitudes of the sensors determined in the manner described above, and from the marks attached to the patient's cranium, the rays to the centers of gravity of the marks are computed. This computation takes into account the information about the imaging characteristics of the optical systems of the sensors, as obtained using the test body. It may be that the computed rays do not intersect exactly. A point which has minimum distance from the two computed rays resulting for the two sensors 34 and 36 is then selected as desired position of a mark.

The coordinates of the marks 22, 24, 26, 28 and 30 determined by the sensors 34 and 36 define the desired position and attitude of the patient's head.

During each subsequent ray treatment, when the patient's head is not exactly aligned and is not rigidly fixed, the position and attitude deviations from the desired position and attitude is continuously computed from the instantaneous coordinates of the centers of gravity of the images of the marks. The position and attitude deviation is described by a translation movement with three translation quantities and a rotation with three angles of rotation.

The computation again uses the inverse function as with the measurement of the position and attitude of the sensors: The centers of gravity of the images of the marks 22, 24, 26, 28 and 30 are computed as functions of the six degrees of freedom of the position and attitude deviations. Minimizing the sum of the squared distances between the computed and measured coordinates of the centers of gravity again results in a system of non-linear equations. This system of equations is solved by liearization and iteration. Thereby optimal values of the position and attitude deviations of the patient's head in the apparatus-fixed coordinate system, and, in particular, of the displacement of the treatment point from the desired position.

The coordinates of the five marks provide the actual position of a "patient-fixed" coordinate system. This actual position and attitude is compared to the "desired position and orientation", which had been determined during the first exact positioning and has been stored in a memory 92. A controller 94 detects the error between actual position and desired position and generates controller output or actuating signals at output terminals 96, 98, and 100. The actuating signals are applied to actuators which are symbolized by block 104 in FIG. 4.

In detail, the following procedure is used:

At first, the imaging characteristics of each individual sensor are determined. This will be explained with reference to FIGS. 6 and 7.

FIG. 6 schematically illustrates a sensor, for example 34. The picture signal generating sensors 34 has the form of a camera with a camera housing 110 and a lens objective 112. The lens objective 112 images a plane test object 114 onto a two-dimensional array 116 of sensor elements. The test object carries a pattern, such as a pattern of concentric circles with a center 118. The test object is placed in such a position relative to the sensor 34 that the optical axis of the sensor 34 passes substantially through the center 118. A corresponding image pattern is generated on the two dimensional array 116 of sensor elements.

Due to aberrations of the lens objective 112, the image will be slightly distorted. This is illustrated in an exaggerated way in FIG. 7. Due to alignment errors, the center 118 may not be imaged not exactly in the center of the array 116 of sensor elements. The center 118 will be imaged on a base point 122. The image of the pattern received by the array 116 of detector elements is referenced to this base point. It will be assumed, that the aberration of the lens objective 112 is rotationally symmetric, thus depends only on the radius referenced to the base point 122. If the imaging were ideal, the characteristic of FIG. 7 would be a straight line 124 extending at 45° to the $r_{gem}$- and $r_{soll}$-coordinate axes. "$r_{gem}$" is the radius of a picture element of the pattern on the test object as "measured" by the sensor elements. "$r_{soll}$" is the radius which should be achieved with ideal imaging characteristics of the lens objective 112. Actually the characteristic 126 in FIG. 7 is slightly curved upwards. The measured radius is slightly smaller than the radius which should be obtained by ideal imaging. The characteristic can be represented by $$r_{soll} = r_{gem} + a_3 \, r_{gem}^3 + a_5 \, r_{gem}^5 + \ldots$$

A point 128 of the pattern will be imaged by the lens objective 112 at the point 130 on the array 116 of detector elements, instead of point 132 which results from the straight line 136 passing through the principal point 134 of the lens objective 112. The point 130 with line 138 would be associated with a point 140.

These corrections are taken into account when computing the visual line to the associated "object element". A brightness value which is measured, for example, at $r_{gem} = 4$ by the respective sensor element, will be associated with a pixel at $r_{soll} = 5$, when computing the visual line, as has been shown—grossly exaggerated- along line 142 in FIG. 7.

Furthermore, the ratio of the ray angle and the picture element coordinates can be taken into account by a factor $sk_y$ and $sk_z$. There is such a factor for each coordinate. A representation is obtained thereby which accurately represents the position of the points in the object plane. The same procedure is applied to sensor 36.

The coefficients $a_3$ and $a_5$ and the factors mentioned before are "internal camera parameters" for the two sensors 34 and 36. They are determined once and are supplied to the computer for the signal processing. Thereby, each sensor element can be associated with a corresponding visual line.

The next step is the initialization of the positions and orientations of the two sensors 34 and 36. The positions and orientations of the sensors 34 and 36 are measured in a coordinate system which is fixed with respect to the ray treatment apparatus 10. Preferably, the origin of the coordinate system coincides with the iso-center 20. One coordinate axis $x_I$ is alignet with the axis of rotation 18 of the ray treatment apparatus, one coordinate axis $z_I$ is vertical, and the third coordinate axis $y_I$ is orthogonal to the coordinate axes $x_I$ and $z_I$. This has been illustrated in FIG. 1.

FIG. 8 shows the coordinate system $x_I$, $y_I$ and $z_I$. A reference body 144 is placed near the iso-center 20 in such a way as to be completely detected by the sensors 34 and 36. The reference body 144 has five marks 145, 146, 148, 150, and 152. These marks 145, 146, 148, 150, and 152 are balls similar to the marks 122 to 128. These balls are "ssen" by the sensors 34 and 36 as circular structures independently of the direction of observation. The position and orientation of the reference body 144 and the positions of the marks 145 to 152 in the coordinate system $x_I$, $y_I$, $z_I$ are exactly known. These positions of the marks are supplied to the computer.

Then the sensors are switched over to the mode of operation of "live pictures". The pictures detected by the sensor elements appear directly on a monitor. By means of these pictures, the sensors can be aligned such that each sensor 34 and 36 detects all five marks 145 to 152. Using the pictures of the marks on the monitor and a cursor moved on these pictures of the marks 145 to 152 by a mouse, the the marks are identified and numbered. Also the pixel values of the centers of gravity of the pictures of the marks can be coarsely determined.

Each of the sensors 34 and 36 provides a picture in which the five marks 145 to 152 appear as circular structures. The centers of gravity of these structures are to be determined. To this end, starting from the pixel which had been selected for a particular mark during the coarse determination of the center of gravity as described above and which clearly is located within the picture of the mark, the locations of the transitions from the, for example, white marks to the dark background are searched line-by-line and column-by-column in both coordinates of the sensor-fixed coordinate system on the basis of the gray values of the picture. This is done by means of a gray value threshold and of a sub-pixel exact gray value interpolation. From the edges thus determined, the center or center of gravity of the picture of the mark is computed separately for each coordinate.

This is well-known picture processing technique and, therefore, is not described in greater detail.

Thus five centers of the pictures of the marks 145 to 152 with two coordinates each in the sensor-fixed coordinate systems are provided by each sensor 34 and 36. In each such coordinate system, two coordinate axes $y_s$ and $z_s$ extend in a plane parallel to the plane of the two-dimensional array 116 (FIG. 6) of sensor elements and parallel to the lines and columns, respectively, thereof. The third coordinate axis $x_s$ extends in the direction of the optical axis 120 of the sensor 34 or 36, respectively. This is schematically shown in FIG. 8.

The centers of the pictures of the marks having the coordinates $y_{si}$, $z_{si}$ (i=1...5) are corrected by means of the internal camera parameters dicussed above.

The position and orientation of the sensors 34 and 36 is defined by six parameters each, namely by the three cartesian coordinates $x_{I1}$, $y_{I1}$, $z_{I1}$ and $x_{I2}$, $y_{I2}$, $z_{I2}$, respectively, and three Eulerian angles $\psi_{I1}$, $\Theta_{I1}$, $\zeta_{I1}$, and $\psi_{I2}$, $\Theta_{I2}$, $\zeta_{I2}$, respectively. The cartesian coordinates of the two sensors 34 and 36 are illustrated in FIG. 8. The cartesian coordinates of a sensor 34 or 36 are the coordinates of the principal point 134 of the lens objective of each sensor 34 or 36, respectively. The cartesian coordinates of the sensors 34 and 36 can be combined in position vectors:

$$\underline{S}_1 = (x_{I1}, y_{I1}, z_{I1}) \text{ and } \underline{S}_2 = (x_{I2}, y_{I2}, z_{I2})$$

The six position and orientation parameters of each sensor 34 and 36 can be combined in vectors:

$$\underline{r}_1 = (x_{I1}, y_{I1}, z_{I1}, \psi_{I1}, \Theta_{I1}, \zeta_{I1})$$

or $$\underline{r}_2 = (x_{I2}, y_{I2}, z_{I2}, \psi_{I2}, \Theta_{I2}, \zeta_{I2}).$$

In these equations, $\zeta_{Im}$ is the rotation about the axis $x_I$ of the apparatus-fixed coordinate system, $\Theta_{Im}$ is the rotation about the axis $y_I$ of the apparatus-fixed coordinate system, $\psi_{Im}$ is the rotation about the axis $z_I$ of the apparatus-fixed coordinate system for the Sensors 34 (m=1) and 36 (m=2).

The three rotations can be described by three transformation matrices or directional cosine matrices, namely $R_z(\psi)$, $R_y(\Theta)$ and $R_x(\zeta)$.
It is:

$$R_Z(\psi_m) = \begin{pmatrix} \cos\psi_m & -\sin\psi_m & 0 \\ \sin\psi_m & \cos\psi_m & 0 \\ 0 & 0 & 1 \end{pmatrix}$$

$$R_Y(\Theta_m) = \begin{pmatrix} \cos\Theta_m & 0 & \sin\Theta_m \\ 0 & 1 & 0 \\ -\sin\Theta_m & 0 & \cos\Theta_m \end{pmatrix}$$

$$R_X(\zeta_m) = \begin{pmatrix} 1 & 0 & 0 \\ 0 & \cos\zeta_m & -\sin\zeta_m \\ 0 & \sin\zeta_m & \cos\zeta_m \end{pmatrix}$$

The total rotation is represented by a matrix:

$$R_m = R_z(\psi_m) \cdot R_y(\Theta_m) \cdot R_x(\zeta_m)$$

These are transformations which transform coordinates from the respective sensor coordinate system $x_{s1}$, $y_{s1}$, $z_{s1}$ for the sensor 34 or $x_{s2}$, $y_{s2}$, $z_{s2}$ into the apparatus-fixed coordinate system. The sensor coordinate system of, for example, sensor 36 can be defined by three unit vectors $\underline{E}_{x2}$, $\underline{E}_{y2}$, $\underline{E}_{z2}$ pointing in the directions of the three coordinate axes $x_{s2}$, $y_{s2}$, $z_{s2}$. In the sensor coordinate system, the three unit vectors have the form:

$$\underline{E}_{X2}^S = \begin{pmatrix} 1 \\ 0 \\ 0 \end{pmatrix}, \underline{E}_{Y2}^S = \begin{pmatrix} 0 \\ 1 \\ 0 \end{pmatrix}, \underline{E}_{Z2}^S = \begin{pmatrix} 0 \\ 0 \\ 1 \end{pmatrix}$$

The same is valid for the coordinate system of sensor 34. In the apparatus-fixed coordinate system $x_I$, $y_I$, $z_I$, this yields:

$$\underline{E}_{X2}^I = R\begin{pmatrix} 1 \\ 0 \\ 0 \end{pmatrix}, \underline{E}_{Y2}^I = R\begin{pmatrix} 0 \\ 1 \\ 0 \end{pmatrix}, \underline{E}_{Z2}^I = R\begin{pmatrix} 0 \\ 0 \\ 1 \end{pmatrix}$$

In the apparatus-fixed coordinate system, $\underline{M}_i$ (i=1...5) is the position vector of the center if the i-th one of the marks 145 to 152. This position vector is exactly known. $\underline{S}_m$ (m=1;2) is the estimated, thus not exactly known position vector of the sensor 34 or 36. Also the matrix R with the trigonometric functions of the Eulerian angles $\psi_m$, $\Theta_m$, $\zeta_m$ is estimated, thus not exactly known. This is, of course, also true with respect to the unit vectors $\underline{E}_{xm}^I$, $\underline{E}_{ym}^I$ and $\underline{E}_{zm}^I$ referenced to the apparatus-fixed coordinate system. The computer calculates, which coordinates the centers of the pictures of the marks 145 to 152 would have in the sensor-fixed coordinate system, assuming such a position and orientation of the sensors 34 and 36. This position and orientation is defined by the equations:

$$\hat{y}_i = sk_y \frac{\underline{E}_{Ym}^I \cdot (\underline{M}_i - \underline{S}_m)}{\underline{E}_{Xm}^I \cdot (\underline{M}_i - \underline{S}_m)}$$

$$\hat{z}_i = sk_z \frac{\underline{E}_{Zm}^I \cdot (\underline{M}_i - \underline{S}_m)}{\underline{E}_{Xm}^I \cdot (\underline{M}_i - \underline{S}_m)}$$

The vector difference $\underline{M}_i - \underline{S}_m$ is the vector from the principal point 134 of the lens objective to a mark "i" of the reference body 144, for example mark 146. Scalar multiplication of this vector difference with the unit vector in $y_s$-direction yields the component of this vector difference in this $y_s$-direction. Scalar multiplication of the vector difference $\underline{M}_i - \underline{S}_m$ with the unit vector $\underline{E}_{xm}^I$ yields the component of the vector difference in the direction of the optical axis of the sensor 34 or 36, respectively. The ratio of the scalar products is approximately the angle which the vector difference forms with the optical axis 120 of the sensor 34 or 36, respectively. Multiplication with the factor $sk_y$ yields the $y_s$-coordinate $y_i$ of the image point calculated with the estimated position and orientation of the sensor 34 or 36.

In similar way the coordinate $z_i$ is calculated.

Observed are the coordinates $y_{i\,korr}$ and $z_{i\,korr}$. These are the cordinates of the sensor elements corresponding to the centers of the images of the marks 145 to 152, corrected -as explained above- for the internal camera parameters.

Error vectors for each sensor 34 or 36 result. These error vectors have the components:

$$f_{iy} = sk_y \cdot \frac{\underline{E}^I_{Ym}(\underline{M}_i - \underline{S}_m)}{\underline{E}^I_{Xm}(\underline{M}_i - \underline{S}_m)} - y_{ikorr}$$

$$f_{iz} = sk_z \cdot \frac{\underline{E}^I_{Zm}(\underline{M}_i - \underline{S}_m)}{\underline{E}^I_{Xm}(\underline{M}_i - \underline{S}_m)} - z_{ikorr}$$

The assumed position $S_m$ and orientation $R_m$ of the sensor 34 and 36 normally is not identical with the true position and orientation. This results in the error vectors mentioned before. In the present case, the looked-for vector $\underline{v}$ has six components. The error vectors provide a total of ten errors. The problem is to purposefully vary the components of the vector $\underline{v}$, thus, for example, the coordinates $x_{l2}$, $y_{l2}$, $z_{l2}$ and the Eulerian angles $\psi_2$, $\Theta_2$ and $\zeta_2$ in the case of sensor 36, such that the errors become zero. This can be done by means of the well-known Newtonian iteration.

From the error vectors, an error function $$F = f_{1y}^2 + f_{2y}^2 + f_{3y}^2 + f_{4y}^2 + f_{5y}^2 + f_{1z}^2 + f_{2z}^2 + f_{3z}^2 + f_{4z}^2 + f_{5z}^2$$

is formed. This error function is to be minimized. This corresponds to a least square fit.

The looked for minimum is defined by the equation

*grad F=0,*

$\underline{0}$ being the zero vector. The components of the error vectors $f_{iy}$ and $f_{iz}$ each is a known function of all components of the position vector $\underline{S}$. Therefore the partial derivatives $$D_{kl} = \frac{\partial f_i}{\partial v_l}$$

can be formed, $v_l$ being the l-th component of the vector $\underline{v}$. Thus in the case of sensor 36, for example, $v_2 = y_{l2}$. This yields a "Jacobi matrix" D, which, in the present case, is a 10×6-matrix. With this Jacobi matrix, an iteration step for the solution of the equation grad F=0 is $$\underline{v}_{(n+1)} = \underline{v}_{(n)} - (D^T \cdot D)^{-1} \cdot D^T \underline{f}$$

In this equation, $\underline{v}_{(n+1)}$ and $\underline{v}_{(n)}$ are the approximations obtained for the vector $\underline{v}$ from the (n+1)st or n-th iteration steps, respectively. $D^T$ is the transposed Jacobi matrix, i.e. a matrix in which in comparison to the matrix D the lines and columns are exchanged. The symbol $^{-1}$ indicates the inverse matrix. And $\underline{f}_{(n)}$ is the error vector after the n-th iteration step.

The iteration is continued until the error vector $\underline{f}_{(n)}$ drops below a preselected threshold. Then the position and orientation of the respective sensor 34 or 36 are known with sufficient accuracy. The procedure described is carried out for both sensors 34 and 36 separately.

The obtained data about the position and orientation of the sensors 34 and 36 are stored. These data are subsequently used for the positioning of patients. The determination of the position and orientation of the sensors is repeated at regular intervals, for example daily.

For the positioning of a patient, four ball-shaped marks 22, 24, 26, 28 are attached, for example, to the patient's head at well-defined positions. During the first measurement, the patient's head is moved by stereotactic methods, as described, into such a position that a tumour to be ray treated is exactly in the iso-center. With this position of the patient's head the positions of the four marks 22, 24, 26 and 28 are measured by the two sensors 34 and 36.

To this end, similar to the procedure with the marks 145, 146, 148, 150 and 152 of the reference body 144, the centers of the images of these marks 22, 24, 26, and 28 are determined. These centers are corrected for the internal camera parameters (FIG. 7), as has been described above with reference to the marks 145, 146, 148, 150, and 152 of the reference body 144. A "visual line" is associated with each of the thus determined, corrected centers. This visual line extends from the respective center through the principal point 134 of the lens objective 112. This visual line should pass through the center of the mark.

At first, the absolute position of each mark 22, 24, 26 and 28 in the apparatus-fixed coordinate system $x_I$, $y_I$, $z_I$ is determined independently. To this end, a start value is determined as "intersection" of the visual lines directed from the two sensors 34 and 36 to one particular mark. Due to measuring inaccuracies the visual lines, in general, will not have an exact intersection. Therefore, the center of the spacing between the visual lines is selected as "intersection".

Now the exact positions of the marks 22, 24, 26, and 28 in the apparatus-fixed coordinate system $x_I$, $y_I$, $z_I$ are determined individually for each mark by means of a Newtonian iteration starting from the start values. The position vector $\underline{P}_j$ of the j-th mark 22, 24, 26 or 28 (j=1 ... 4) in the coordinate system $x_I$, $y_I$, $z_I$ is $$P_j(\hat{x}_j, \hat{y}_j, \hat{z}_j).$$

The errors, i.e. the deviations of the calculated and observed positions of the image of the mark in the sensor-fixed coordinate system of the first sensor 34 (m=1) are $$f_{y1} = sk_{y1} \cdot \frac{\underline{E}^I_{Y1} \cdot (P_i - S_1)}{\underline{E}^I_{X1} \cdot (P_i - S_1)} - Y^i_{1korr}$$

$$f_{z1} = sk_{z1} \cdot \frac{\underline{E}^I_{Z1} \cdot (P_i - S_1)}{\underline{E}^I_{X1} \cdot (P_i - S_1)} - Z^i_{1korr}$$

In the same way, the errors for the second sensor 36 (m=2) in the sensor-fixed coordinate system are:

$$f_{y2} = sk_{y2} \cdot \frac{\underline{E}^I_{Y2}(P_i - S_2)}{\underline{E}^I_{X2}(P_i - S_2)} - y^i_{2korr}$$

$$f_{z2} = sk_{z2} \cdot \frac{\underline{E}^I_{Z2}(P_i - S_2)}{\underline{E}^I_{X2}(P_i - S_2)} - z^i_{2korr}$$

In these equations -similar to the measurement of the position and orientation of the sensors 34 and 36 by means of the test body 144- $S_1$ and $S_2$ are position vectors of the sensors 34 and 36, and $y_{m\,korr}$ and $z_{m\,korr}$ are the observed coordinates of the pictures of the marks 145 to 152 in the sensor-fixed coordinate system corrected for the internal camera parameters. The errors, again, are known functions of the estimated position coordinates $x_j$, $y_j$, $z_j$ ($P_1$, $P_2$, $P_3$). The errors can be combined to an error vector $$f = (f_{y1}{}^i, f_{z1}{}^i, f_{y2}{}^i, f_{z2}{}^i) = (f_1, f_2, f_3, f_4)$$

Then a Jacobi matrix D* having the Elements $$D^*{}_{ik} = \frac{\partial f_i}{\partial P_k}$$

can be formed. In this case, the Jacobi matrix is a 4×3-matrix.

A Newtonian iteration $$\underline{P}_{j(n+1)} = \underline{P}_{j(n)} - (D^{*T} * D^*)^{-1} * D^{*T} f$$

yields the position vectors of the marks 22, 24, 26 and 28 in the apparatus-fixed coordinate system $x_I$, $y_I$, $z_I$.

An "inherent coordinate system" $x_E$, $y_E$, $z_E$ is defined by the positions of the four marks 22, 24, 26, 28 thus obtained. The origin of this inherent coordinate system coincides with the center of gravity 30 of the four marks 22, 24, 26 and 28. The unit vector pointing into the $z_E$-direction is the normalized vector product of the two vectors which interconnect the centers of the marks 24 and 26 and of the marks 28 and 22, respectively (FIG. 9). Thus this unit vector and the z-axis are orthogonal to the paper plane of FIG. 9 and are directed into this paper plane. The unit vector pointing into the direction of the $y_E$-axis is parallel to the connecting line 158 between the centers of the marks 22 and 28. The $y_E$-axis points to the left in FIG. 9. The unit vector pointing into the direction of the $x_E$-axis forms a righthand system with the unit vectors of the $y_E$- and $z_E$-axes and points downwards in FIG. 9.

The data $\underline{P}_j$ thus obtained are stored. If the marks 22, 24, 26 and 28 are exactly in this position, the tumour will be exactly in the iso-center 20.

When a subsequent ray treatment is to be made, the coordinates of the marks 22, 24, 26 and 28 stored during the stereotactic positioning of the patient's head are available. Now the position and orientation of the patient's head relative to these fixed coordinates has to be continuously determined. This is achieved, again, by means of a Newtonian iteration.

In this case, a vector $$\underline{k} = (\Delta X_k, \Delta Y_k, \Delta Z_k, \Delta\psi_k, \Delta\Theta_k, \Delta\zeta_k)$$

is to be found. Components of this vector are the deviations of the position and orientation of the head-fixed inherent coordinate system defined by the marks 22, 24, 26 and 28 from the position and orientation in which the patient's head was held in a position and orientation fixed by stereotactic methods with the tumour in the iso-center 20, and which had been determined in the manner described above and which has been stored.

The position of the head and of the head-fixed inherent coordinate system can be defined by a translation vector $$\underline{t} = (\Delta x_k, \Delta y_k, \Delta z_k)$$

The orientation of the head and of the head-fixed coordinate system $x_E$, $y_E$, $z_E$ relative to the apparatus-fixed coordinate system $x_I$, $y_I$, $z_I$ can be defined by a directional cosine matrix $R_k$ as a function of the Eulerian angles $\Delta\psi_k$, $\Delta\Theta_k$, $\Delta\zeta_k$.

$$R_k = R_{kx}(\Delta\psi_k) * R_{ky}(\Delta\Theta_k) * R_{kz}(\Delta\zeta_k)$$

analog to the directional cosine matrix for fixing the orientation of the sensor 36.

The errors in the sensor-fixed coordinate system for the four marks 22, 24, 26, and 28 (j=1 ... 4) and for the sensor 34 (m=1) are:

$$f_{y1}^i = sk_{y1} \cdot \frac{\underline{E}_{Y1}^I \cdot (R_k \cdot \underline{P}_i + \underline{t}) - \underline{S}_1)}{\underline{E}_{X1}^I \cdot (R_k \cdot \underline{P}_i + \underline{t}) - \underline{S}_1)} - Y_{1korr}^i$$

$$f_{z1}^i = sk_{z1} \cdot \frac{\underline{E}_{Z1}^I \cdot (R_k \cdot \underline{P}_i + \underline{t}) - \underline{S}_1)}{\underline{E}_{X1}^I (R_k \cdot \underline{P}_i + \underline{t}) - \underline{S}_1)} - Z_{1korr}^i$$

Correspondingly, the sensor 36 (m=2) provides errors:

$$f_{y2}^i = sk_{y2} \cdot \frac{\underline{E}_{Y2}^I (R_k \cdot \underline{P}_i + \underline{t}) - \underline{S}_2)}{\underline{E}_{X2}^I (R_k \underline{P}_i + \underline{t}) - \underline{S}_2)} - Y_{2korr}^i$$

$$f_{z2}^i = sk_{z2} \cdot \frac{\underline{E}_{Z2}^I (R_k \underline{P}_i + \underline{t}) - \underline{S}_2)}{\underline{E}_{X2}^I (R_k \underline{P}_i + \underline{t}) - \underline{S}_2)} - Z_{2korr}^i$$

In these equations, $R_k \underline{P}_j$ represents the position vector of the j-th mark (22, 24, 26 or 28) rotated through the Eulerian angles $\Delta\psi_k$, $\Delta\Theta_k$, $\Delta\zeta_k$. The translation $\underline{t}$ is superimposed to position vector thus rotated. This provides an estimated value of the position of each of the marks 22, 24, 26 or 28 from an estimated directional cosine matrix and an estimated translation vector $\underline{t}$. The difference with the vector $\underline{S}_1$ or $\underline{S}_2$ provides the vector from the principal point 134 of the lens objective 112 to the mark "j", thus 22, 24, 26 or 28. The scalar products of his vector difference with the unit vectors $\underline{E}_{ym}$ or $\underline{E}_{zm}$ and with the unit vectors $\underline{E}_{xm}$ are formed. The ratios provide angles which, multiplied by a scale factor $sk_{ym}$ or $sk_{zm}$, respectively, provide the calculated coordinates of the images of the marks 22, 24, 26 or 28 on the array 116 of sensor elements. The difference with the coordinates of the actually observed images (with correction for the internal camera parameters) provide the errors.

With two sensors 34 and 36 (m=1;2) and four marks 22, 24, 26 and 28 (j=1 ... 4) having two coordinates each, the error vector $\underline{f}$ has sixteen components. The sixteen components of the error vector $\underline{f}$ are known functions of the vector $\underline{k}$. Again a Jacobi matrix D' can be formed from the partial derivatives of the components of the error vector $\underline{f}$ with respect to a respective on of the components of the vector $\underline{k}$. Such a Jacobi matrix is a 16×6-matrix.

At first, for carrying out a Newtonian iteration, estimated values of the positions of the marks 22, 24, 26 and 28 are calculated as intersections of two visual lines each. The origin and the directions of the coordinates of the inherent coordinate system $x_E$, $y_E$, $z_E$ of the marks 22, 24, 26 and 28 can be derived from these estimated values. From the current inherent coordinate system thus calculated and the stored inherent coordinate system determined during the original positioning, the rotation and translation of the position and oriantation changes are derived. This is the transformation which transforms the inherent coordinate system of the original positioning into the current inherent coordinate system. This yields components of the vector $\underline{k}$ as start values.

Subsequently, starting from the start values of the vector $\underline{k}$, the true components of the vector $\underline{k}$ are computed by means of the Newtonian iteration described above.

The operations described above are repeated cyclically, whereby continuously the current vector $\underline{k}$ is available. The result of each cycle serves as start value for the next following cycle.

As illustrated schematically in FIG. 1, the patient lies on a carriage 15 which is guided for horizontal, longitudinal movement on a ray treatment table 16. The patient's head lies on a head rest 108. The head rest 108 is vertically and transversely movable relative to the carriage 15. An actuator 160 serves to adjust the head rest 108 in transverse direction. An actuator 162 serves to adjust the head rest 108 vertically. There is no longitudinal adjustment of the head rest 108 relative to the carriage 15, as such adjustment would cause the patient's neck to be extended or compressed. Instead, the carriage 15 is adjusted longitudinally by an actuator 164. The patient's head can be fixed on the head rest 108 by conventional means. Movements, if any, are compensated for by the control loops. The treatment point in the patient's head remains in the iso-center 20 with high accuracy.

The described device can be modified in various ways. It can be used to treat some other body part instead of the patient's head and cranium. Three sensors can be provided instead of the two sensors 34 and 36. In the case of over-determination, the coordinates can be computed from the computed rays in accordance with the least square method.

We claim:

1. A device for positioning a body part of the human body for treatment with a medical apparatus, wherein marks are affixed to said body part at well-defined positions, the positioning of said body part causing an exactly defined treatment point to be maintained at a desired position, characterized by
   (a) at least two picture signal generating sensors (34,36), which are aligned to monitor said marks (22,24,26,28.30),
   (b) picture processing means (74,76), to which said picture signals from said sensors (34,36) are applied for processing pictures (54A to 62A;54B to 62B) of said marks to fix marker points (80), which are determined by said marks and define the actual position of said body part,
   (c) signal processing and controller means (86,88,90;92,94)
   for computing the actual position of the body part from the observed position of said marker points,
   for comparing said actual position with a desired position, and
   for generating actuating signals, which depend on the error between said actual position and said desired position of said body part, and
   (d) means for preventing treatment with misalignment between said apparatus and said body part, said actuating signals being applied to said preventing means.

2. A device as claimed in claim 1, wherein said preventing means comprise actuator means (102,104,106) to which said actuating signals are applied and which are arranged to restore the proper alignment between said apparatus and said body part, if said body part has deviated from its desired position.

3. A device as claimed in claim 2, wherein said actuator means (102,104,106) are arranged to engage said body part to return said body part to said desired position, if it has deviated from this desired position.

4. A device as claimed in claim 1, wherein
   (a) each of said picture signal generating sensors (34,36) comprises means for generating a pixel matrix (50,52), in which the marks appear as two-dimensional structures (54A to 62A; 54B to 62B), and
   (b) said picture processing means comprising means for determining the centers of gravity (80) of the two-dimensional structures, said centers of gravity representing said marker points.

5. A device as claimed in claim 4, wherein said marks (22,24,26,28,30) are balls, which, in the pixel matrix, appear as circular structures (54A to 62A; 54B to 62B) independently of the direction from which they are observed.

6. A device as claimed in claim 5 wherein areas (32) forming a contrast with said balls are provided behind said balls, as viewed from said sensors.

7. A device as claimed in claim 5 and further comprising means for illuminating said balls from a plurality of directions.

8. A device as claimed in claim 1, wherein at least three marks (22,24,26,28,30) are provided.

9. A device as claimed in claim 1, and further including actuator means for angularly aligning said body part.

10. A device for accurately positioning a patient's head for treatment with a ray treatment apparatus, wherein marks are affixed to said head at well-defined positions, the positioning of said head causing a tumour, which is to be ray treated, to be maintained at a desired position, characterized by
   (a) at least two picture signal generating sensors (34,36), which are aligned to monitor said marks (22,24,26,28.30),
   (b) picture processing means (74,76), to which said picture signals from said sensors (34,36) are applied for processing pictures (54A to 62A;54B to 62B) of said marks to fix marker points (80), which are determined by said marks and define the actual position of said head,
   (c) signal processing and controller means (86,88,90;92,94)
   for computing the actual position of said head from the observed position of said marker points,
   for comparing said actual position with a desired position, and
   for generating actuating signals, which depend on the error between said actual position and said desired position of said head,
   (d) an elongated ray treatment table (16) defining a longitudinal direction and a carriage guided on said ray treatment table for horizontal movement in said longitudinal direction, said ray treatment table being adapted to accommodate a patient,
   (e) a head rest (108) separate from said ray treatment table (16) and carriage and adapted to accommodate the patient's head and means for fixing the patient's head on said head rest (108),
   (f) first and second actuator means (104,102), to which respective ones of said actuating signals are applied, for engaging said head rest (108) to move said head rest relative to said ray treatment table (16) and (g) a third actuator means, to which a third one of said actuating signals is applied and which engages said carriage to move said carriage in said longitudinal direction, (h) said actuator means being arranged and controlled by said actuating signals to to return said patient's head to said desired position, if it has deviated from this desired position.

11. A device as claimed in claim 10 and further including actuator means for angularly aligning said head rest.

12. A method for for positioning a body part of the human body for treatment with a medical apparatus, wherein marks are affixed to said body part at well-defined positions, the positioning of said body part causing an exactly defined treatment point to be maintained at a desired position, characterized by the method steps of (a) measuring the position of said marks by means of at least two picture generating sensors during a first treatment, when said body part to be treated is fixed in a predetermined desired position relative to said medical apparatus, whereby said sensors produce two-dimensional pictures of said marks, (b) determining the centers of gravity of said images by picture processing in sensor-fixed coordinate systems, (c) determining the position of said centers of gravity of said marks in an apparatus-fixed coordinate system from the centers of gravity of the pictures as a measure of a desired position of said body part, (d) measuring the position of said marks during a subsequent treatment by means of the same sensors which are aligned in the same way as during said first treatment, (e) determining the position deviation of the centers of gravity of the marks in the apparatus-fixed coordinate-system from the centers of gravity said pictures determined in said sensor-fixed coordinate systems, and (f) generating actuating signals depending on said position deviation and correcting the position of said body part in response to said actuating signals.

13. A method as claimed in claim 12 wherein said picture generating sensors comprise an imaging optical system and the positions of marks provided a test body are measured by said picture generating sensors, whereby the imaging characteristics of the optical systems of said picture generating sensors are calibrated.

14. A method as claimed in claim 12, wherein marks provided on a reference body and having a well-defined position and attitude in the apparatus-fixed coordinate system is measured by said sensors, the position and attitude of said sensors in said apparatus-fixed coordinate system being determined from the positions of said pictures detected by said sensors.

* * * * *